United States Patent [19]

Davidson et al.

[11] Patent Number: 5,614,182
[45] Date of Patent: Mar. 25, 1997

[54] METHODS OF ATTRACTING AND COMBATTING INSECTS

[75] Inventors: Thomas C. Davidson, Pelham; Georgina M. Werner, Raleigh, both of N.C.

[73] Assignee: Rhone-Poulenc Inc., Research Triangle Park, N.C.

[21] Appl. No.: 419,609

[22] Filed: Apr. 10, 1995

[51] Int. Cl.$^6$ .................................................. A01N 25/00
[52] U.S. Cl. .................................................. 424/84
[58] Field of Search .................................................. 424/84

[56] References Cited

U.S. PATENT DOCUMENTS 5,232,940  8/1993  Hatton et al. .............................. 514/407

FOREIGN PATENT DOCUMENTS

| | | |
|---|---|---|
| 0295117 | 12/1988 | European Pat. Off. . |
| 87/03781 | 7/1987 | WIPO . |
| 93/06089 | 4/1993 | WIPO . |
| 94/21606 | 9/1994 | WIPO . |

*Primary Examiner*—Brian M. Burn
*Attorney, Agent, or Firm*—Burns, Doane, Swecker & Mathis, L.L.P.

[57] ABSTRACT

Use of 1-[$R^2R^1R^3$phenyl]-3-CN-4-[$S(O)_nR^4$]-5-$R^5$-pyrazoles as insect attractants.

28 Claims, No Drawings

METHODS OF ATTRACTING AND COMBATTING INSECTS

BACKGROUND OF THE INVENTION

1. Field of the Invention

The invention relates to methods of attracting and combatting insects at a locus at which a crop is growing, especially a plantation crop, or at a locus where the presence of insects is undesirable for public health reasons.

2. Description of the Related Art

Many insecticidally active compounds are known, such as the insecticidal pyrazoles described in International Patent Publications No. WO 87/03781, WO 93/06089 and WO 94/21606, as well as in European Patent Publication No. 0295117 and Hatton et al U.S. Pat. No. 5,232,940.

A particular problem connected with the control of insects, especially the insects which are found to inhabit private or public housing or buildings, is that it is rather difficult to reach and treat all of the insects and it is most desirable to have a method to eliminate the population of insects, especially those insects which are not accessible to the treatment or have failed to be treated for any reason.

An additional obstacle in eliminating or reducing a population of insects is that the insects are often able to detect the presence of insecticidally active ingredients, which ingredients therefore can act as a repellent or anti-feeding agent for the insects.

Up until now, a common method for controlling a large population of insects, especially those inaccessible to direct treatment, is to have multiple treatments or multiple placement of baits containing insecticidally active ingredients, or to associate attractants with insecticidally active ingredients.

OBJECTS AND SUMMARY OF THE INVENTION

An object of the instant invention is to provide a simplified and efficient method of controlling or combatting insects.

A further object of the instant invention is to provide a simplified and efficient method of controlling or combatting insects whereby an attractive ingredient, that is, an attractant, is presented to the insects.

A further object of the instant invention is to provide a simplified and efficient method of controlling or combatting insects whereby an attractant is presented to the insects, said attractant being simultaneously insecticidally active.

The present invention thus provides a new use, as an attractant for insects, of a compound having the formula:

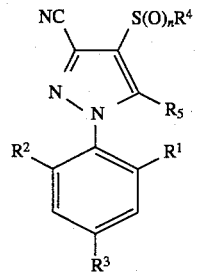

wherein:

each of $R^1$ and $R^2$, which are the same or different, is a hydrogen or halogen atom, at least one of them preferably being other than hydrogen;

$R^3$ is a halogen atom or a haloalkyl, haloalkoxy or $SF_5$ radical;

$R^4$ is an alkyl or haloalkyl radical;

$R^5$ is an alkyl, haloalkyl, amino, alkylamino or dialkylamino radical; and n is 0, 1 or 2.

In one aspect, the present invention thus provides a method for attracting insects, said method comprising offering to said insects for ingestion an effective attractant amount of a compound of formula (I) as defined above.

In another aspect, the present invention provides a method for attracting and killing insects comprising offering to said insects for ingestion a compound of formula (I) as defined above in an amount which is effective both as an attractant and as an insecticide.

DETAILED DESCRIPTION OF THE INVENTION

In the present description, the following definitions are applicable:

The alkyl radicals and the alkyl portions of the haloalkyl, haloalkoxy, alkylamino and dialkylamino radicals can have up to seven carbon atoms but are preferably lower alkyl, that is to say, they preferably each have one to four carbon atoms. In the case of the dialkylamino radicals, the alkyl portions can be the same or different.

Preferred compounds of formula (I) for use in accord with the present invention are compounds in which each of $R^1$ and $R^2$ is a halogen atom, $R^3$ is a haloalkyl radical, $R^4$ is a lower haloalkyl radical and $R^5$ is an amino radical.

Especially preferred for use in accord with the present invention is the insecticide known as fipronil, whose chemical name is 5-amino-3-cyano-1-(2,6-dichloro-4-trifluoromethyl)phenyl-4-trifluoromethylsulfinylpyrazole, and which is specifically described in the aforementioned EP 0295117 and Hatton et al U.S. Pat. No. 5,232,940.

The preparation of compounds of formula (I) for use herein can proceed according to any process described in the hereinabove-cited patent documents, or other process within the knowledge of one skilled in the art of chemical synthesis.

According to a further aspect of the invention, there is provided a method for controlling a population of insects, especially insects able to walk or travel in public or private housing or building or household or home, that is, insects which are able to enter or inhabit buildings, whereby an attractant and insecticidally effective amount of a compound of formula (I) as defined above is offered or presented to the insects to be controlled as food among alternative food or foods, which can be closely situated.

The method of the invention is especially advantageous because it provides more possibilities and much more freedom for placement of the insecticidally active ingredient. Because of its attractant properties, the insecticidally active ingredient can be located in any place, not only at the specifically appropriate place where the insects are to travel and feed.

In a preferred embodiment of the present invention, there is provided a method for controlling a population of insects at a locus which is in or near a food storage, preparation, serving or eating area, said method comprising offering to said insects as an alternative food source an amount of a compound of formula (I) as defined above which is effective both as an attractant and as an insecticide. Thus, an effective attractant and insecticidal amount of a compound of formula (I) is preferably offered to the insects in or near an area in which other food is present as a practical consequence of the normal use of the building or housing.

The active ingredient of formula (I) is preferably used in accord with the present invention in the form of a bait, which can be a solid, liquid or gel bait. The manner of preparation of a bait will be apparent to one of ordinary skill in the art. Baits have already been described in the patent documents cited hereinabove. It is of course not necessary to add an attractant to the active ingredient of formula (I) and the carrier or diluent to form the bait, since the compound of formula (I) acts herein as an attractant as well as an insecticide.

The method of the invention is particularly appropriate as a method for the control of populations of insects like cockroaches, ants or the like. Treatment of cockroaches in an area in which their presence can be detrimental to public health, that is to say in housing or buildings, is a preferred feature of the instant invention, especially for the control of so-called American cockroaches (*Periplanipa americana*), but also of other cockroaches such as German cockroaches (*Blatella germanica*).

The attractant compositions or baits which can be used in the practice of the present invention can be offered or presented to the insects in various amounts. Usually, however, it is advantageous to offer these attractant compositions or baits comprising the compound of formula (I) in an appropriate form and in an amount of from about 0.00001 g to about 20 g of active ingredient of formula (I) per 100 square meters, preferably of from about 0.001 g to about 1 g per 100 m$^2$.

The attractant compositions which are useful in the present invention generally comprise from about 0.0001 to about 15% w/w of active ingredient of formula (I), preferably from about 0.01 to about 6% w/w. These compositions can be in the form of a solid, e.g. dusts or granules or wettable powders, or in the form of a liquid, such as an emulsifiable concentrate or a true solution.

The attractant compositions can also contain any compatible surface-active agent and/or carrier, preferably selected from ingredients which can be eaten by insects. The carrier itself can be solid or liquid.

The compounds of formula (I) can be used in sequence or admixture, particularly in admixtures with another pesticide, for example, an insecticide, acaricide or fungicide.

The attractant compositions can be prepared by simply admixing the ingredients.

The invention is illustrated by the following examples which should not be considered as limiting or restricting the invention.

EXAMPLES

On a large circle situated on a 1 square meter confinement, various foodstuffs and two baits of fipronil were distributed around the perimeter of a circle of 75 cm diameter. Similar pieces of baits were placed at diametrically opposed points on the circle.

Adults cockroaches (25 males and 25 females) were released and offered harborage 24 hours prior to the start of the experiment. All testing was conducted at night under infrared illumination. Three replicates were conducted for each species. Observations began one hour after lighting in the laboratory went off. The number of foraging cockroaches at each location was recorded at 10 minute intervals for a period of 120 minutes.

Example 1

Only fipronil was used as an insecticide.

The alternative foods were: 2 pieces of rodent chow, 2 pieces of rodent jelly and 2 vials of water.

The numbers of foraging German cockroaches for up to 3 hour of foraging time were measured and cumulatively added.

62 cockroaches went to fipronil, 43 to chow, 25 to jelly and 22 to water.

Example 2

Only fipronil was used as an insecticide.

The alternative foods were: 2 pieces of rodent chow, 2 vials of oil and 2 vials of water.

The numbers of foraging German cockroaches for up to 3 hours of foraging time were measured and cumulatively added.

68 cockroaches went to fipronil, 25 to chow, 23 to oil and 14 to water.

Example 3

One insecticidal bait comprised fipronil and one comprised hydramethylnon.

The alternative foods were: 2 pieces of rodent chow, 2 pieces of rodent jelly, 2 vials of water and 1 piece of hydramethylnon.

The numbers of foraging American cockroaches for up to 3 hours of foraging time were measured and cumulatively added.

35 cockroaches went to fipronil (substantially less to the other insecticide), 17 to chow, 15 to jelly and 18 to water.

While the invention has been described in terms of various preferred embodiments, the skilled artisan will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A method for attracting insects, said method comprising offering to said insects for ingestion an effective attractant amount of a compound having the formula:

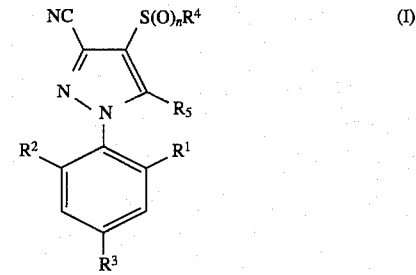

wherein:
each of $R^1$ and $R^2$, which are the same or different, is a hydrogen or halogen atom;

$R^3$ is a halogen atom or a haloalkyl, haloalkoxy or $SF_5$ radical;

$R^4$ is an alkyl or haloalkyl radical;

$R^5$ is an alkyl, haloalkyl, amino, alkylamino or dialkylmnino radical; and n is 0, 1 or 2.

2. The method according to claim 1, wherein at least one of $R^1$ and $R^2$ is a halogen atom.

3. The method according to claim 2, wherein each of $R^1$ and $R^2$ is a halogen atom, $R^3$ is a haloalkyl radical, $R^4$ is a lower haloalkyl radical and $R^5$ is an amino radical.

4. The method according to claim 3, wherein the compound of formula (I) is 5-amino-3-cyano-1-(2,6-dichloro-4-trifluoromethyl)phenyl-4-trifluoromethylsulfinylpyrazole.

5. The method according to claim 1, wherein said insects are insects which are able to enter or inhabit buildings.

6. The method according to claim 5, wherein said compound of formula (I) is offered to said insects as an alternative food source at a locus which is in or near an area in which other food is present.

7. The method according to claim 6, wherein the food source comprising said compound of formula (I) is in solid form.

8. The method according to claim 7, wherein said solid form is a solid bait.

9. The method according to claim 6, wherein said insects are cockroaches.

10. The method according to claim 6, wherein said compound of formula (I) is offered in an amount of from about 0.00001 g to about 20 g per 100 square meters.

11. The method according to claim 10, wherein said compound of formula (I) is offered in an amount of from about 0.001 g to about 1 g per 100 square meters.

12. The method according to claim 6, wherein the food source comprising said compound of formula (I) comprises from about 0.001 to about 15% w/w of compound of formula (I).

13. The method according to claim 12, wherein the food source comprising said compound of formula (I) comprises from about 0.1 to about 6% w/w of compound of formula (I).

14. A method for attracting and killing insects comprising offering to said insects for ingestion a compound having the formula:

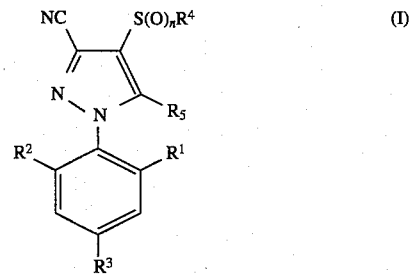

wherein:
each of $R^1$ and $R^2$, which are the same or different, is a hydrogen or halogen atom;
$R^3$ is a halogen atom or a haloalkyl, haloalkoxy or $SF_5$ radical;
$R^4$ is an alkyl or haloalkyl radical;
$R^5$ is an alkyl, haloalkyl, amino, alkylamino or dialkylamino radical; and
n is 0, 1 or 2;
wherein said compound of formula (I) is offered in an amount which is effective both as an attractant and as an insecticide.

15. The method according to claim 14, wherein at least one of $R^1$ and $R^2$ is a halogen atom.

16. The method according to claim 15, wherein each of $R^1$ and $R^2$ is a halogen atom, $R^3$ is a haloalkyl radical, $R^4$ is a lower haloalkyl radical and $R^5$ is an amino radical.

17. The method according to claim 16, wherein the compound of formula (I) is 5-amino-3-cyano-1-(2,6-dichloro-4-trifluoromethyl)phenyl-4-trifluoromethylsulfinylpyrazole.

18. A method for controlling a population of insects at a locus which is in or near a food storage, preparation, serving or eating area, said method comprising offering to said insects as an alternative food source an amount of a compound having the formula:

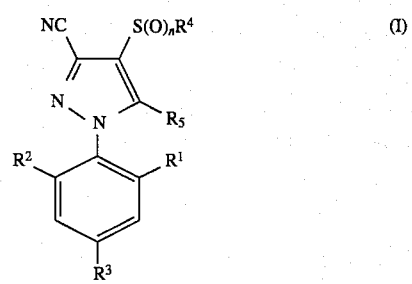

wherein:
each of $R^1$ and $R^2$, which are the same or different, is a hydrogen or halogen atom;
$R^3$ is a halogen atom or a haloalkyl, haloalkoxy or $SF_5$ radical;
$R^4$ is an alkyl or haloalkyl radical;
$R^5$ is an alkyl, haloalkyl, amino, alkylamino or dialkylamino radical; and
n is 0, 1 or 2;
which is effective both as an attractant and as an insecticide.

19. The method according to claim 18, wherein at least one of $R^1$ and $R^2$ is a halogen atom.

20. The method according to claim 19, wherein each of $R^1$ and $R^2$ is a halogen atom, $R^3$ is a haloalkyl radical, $R^4$ is a lower haloalkyl radical and $R^5$ is an amino radical.

21. The method according to claim 20, wherein the compound of formula (I) is 5-amino-3-cyano-1-(2,6-dichloro-4-trifluoromethyl)phenyl-4-trifluoromethylsulfinylpyrazole.

22. The method according to claim 18, wherein the food source comprising said compound of formula (I) is in solid form.

23. The method according to claim 22, wherein said solid form is a solid bait.

24. The method according to claim 18, wherein said insects are cockroaches.

25. The method according to claim 18, wherein said compound of formula (I) is offered in an amount of from about 0.00001 g to about 20 g per 100 square meters.

26. The method according to claim 25, wherein said compound of formula (I) is offered in an amount of from about 0.001 g to about 1 g per 100 square meters.

27. The method according to claim 18, wherein the food source comprising said compound of formula (I) comprises from about 0.001 to about 15% w/w of compound of formula (I).

28. The method according to claim 27, wherein the food source comprising said compound of formula (I) comprises from about 0.1 to about 6% w/w of compound of formula (I).

* * * * *

(12) EX PARTE REEXAMINATION CERTIFICATE (7769th)
United States Patent
Davidson et al.

(10) Number: US 5,614,182 C1
(45) Certificate Issued: Sep. 28, 2010

(54) METHODS OF ATTRACTING AND COMBATTING INSECTS

(75) Inventors: Thomas C. Davidson, Pelham, NC (US); Georgina M. Werner, Raleigh, NC (US)

(73) Assignee: Rhone Poulenc Inc., Research Triangle Park, NC (US)

Reexamination Request:
No. 90/008,320, Dec. 12, 2006

Reexamination Certificate for:
Patent No.: 5,614,182
Issued: Mar. 25, 1997
Appl. No.: 08/419,609
Filed: Apr. 10, 1995

(51) Int. Cl.
*A01N 43/56* (2006.01)
*A01N 43/48* (2006.01)
*A01N 47/02* (2006.01)

(52) U.S. Cl. .................................................. 424/84
(58) Field of Classification Search .................. None
See application file for complete search history.

(56) References Cited

U.S. PATENT DOCUMENTS

| 4,911,907 | A | 3/1990 | Shimamura et al. |
| 5,232,940 | A | 8/1993 | Hatton |
| 5,296,220 | A | 3/1994 | Roelofs et al. |
| 5,505,951 | A | 4/1996 | Roelofs et al. |

FOREIGN PATENT DOCUMENTS

| EP | 0234119 | 9/1987 |
| EP | 0295117 | 12/1988 |
| GB | 950498 | 12/1986 |
| PL | 158243 | 10/1988 |
| PL | 153578 | 3/1989 |

OTHER PUBLICATIONS

Wang, C. and G.W. Bennet, Comparison of cockroach traps and attractants for monitoring German cockroaches (Dictyoptera: Blattellidae). Environ. Entomol. 35:765–770, 2006.
Maple Lactone (2–cyclopenten–1–one, 2–hydroxy–3–methyl) (004049) Fact Sheet. [online], [retrieved on Apr. 27, 2010]. Retrieved from the Internet <http://www.epa.go/pesticides/biopesticides/ingredients/factsheets/factsheet–004049.htm >.
Dethier, V.G., et al., "The Designation of Chemical in Terms of the Responses They Elicit from Insects," J. Econ. Entomol. 53:134–136, 1960.
Miller, J.R., et al., "Designation of Chemicals in Terms of the Locomotor Responses They Elicit from Insects: An Update of Dethier et al. (1960)," j. Econ. Entomol. 102(6):2056–2060, 2009.
Proof 2, Monograph The Merck Index, 14$^{th}$ Ed., 2006, No. 4085 (No. Cas 120068–37–3).
Proof 3, V. Durier and C. Rivault, An original and a sworn translation from English language, Medical and Veterinary Ensomology, pp. 410–418.
Proof 4, Journal of Economic Entohology, vol. 97, No. 6, p. 2070.
F.A.M. Mariconi, et al., "Testing of Products to Fight Mound Building Termites," Sci. agric., Piracicaba, 51(3):505–508 (Sep./Dec. 1994) and English translation.
F. Colliot, et al., "Fipronil: A New Soil and Foliar Broad Spectrum Insecticide," Brighton Crop Protection Conference—Pests and Diseases(1992.

*Primary Examiner*—Dwayne C Jones

(57) ABSTRACT

Use of 1-[$R^2R^1R^3$phenyl]-3-CN-4-[$S(O)_nR^4$]-5-$R^5$-pyrazoles as insect attractants.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-7 and 14-22 are cancelled.
Claims 8-13 and 23-28 are determined to be patentable as amended.

8. [The method according to claim 7, wherein said solid form is a solid bait.] *A method for attracting insects, said method comprising offering to said insects for ingestion an effective attractant amount of a compound having the formula:*

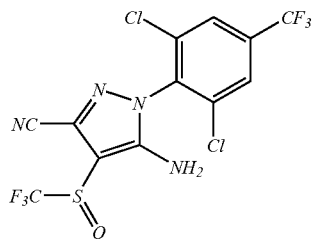

*wherein the compound is 5-amino-3-cyano-1-(2,6-dichloro-4-trifluoromethyl)phenyl-4-trifluoromethylsulfinylpyrazole; wherein said compound is offered to said insects as an alternative solid food source at a locus which is in or near an area in which other food is present; and wherein said alternative solid food source is a bait comprising said compound and ingredients that can be eaten by insects, but said bait does not contain an additional attractant.*

9. The method according to claim [6] *8*, wherein said insects are cockroaches.

10. [The method according to claim 6, wherein said compound of formula (I) is offered in an amount of from about 0.00001 g to about 20 g per 100 square meters.] *The method according to claim 9, wherein said compound is present in said bait in an amount of from about 0.00001 g to about 20 g per 100 square meters.*

11. [The method according to claim 10, wherein said compound of formula (I) is offered in an amount of from about 0.001 g to about 1 g per 100 square meters.] *The method according to claim 10, wherein said compound is present in said bait in an amount of from about 0.001 g to about 1 g per 100 square meters.*

12. [The method according to claim 6, wherein the food source comprising said compound of formula (I) comprises from about 0.0001 to about 15w/w of compound of formula (I).] *The method according to claim 8, wherein said bait comprises from about 0.001 to about 15% w/w of said compound.*

13. [The method according to claim 12, wherein the food source comprising said compound of formula (I) comprises from about 0.1 to about 6% w/w of compound of formula (I).] *The method according to claim 12, wherein said bait comprises from about 0.1 to about 6% w/w of said compound.*

23. [The method according to claim 22, wherein said solid form is a solid bait.] *A method for controlling a population of insects at a locus which is in or near a food storage, preparation, serving or eating area, said method comprising offering to said insects as an alternative food source an amount of a compound having the formula:*

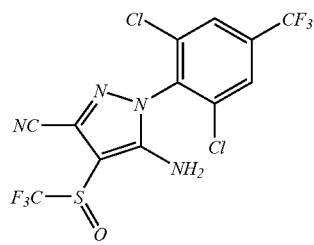

*wherein the compound is 5-amino-3-cyano-1-(2,6 dichloro-4-trifluoromethyl)phenyl-4-trifluoromethylsulfinylpyrazole, which is effective both as an attractant and as an insecticide without additional attractant components; and wherein said alternative food source is a solid bait comprising said compound and ingredients that can be eaten by insects, but said bait does not contain an additional attractant.*

24. The method according to claim [18] *23*, wherein said insects are cockroaches.

25. [The method according to claim 18, wherein said compound of formula (I) is offered in an amount of from about 0.00001 G to about 20 g per 100 square meters.] *The method according to claim 23, wherein said compound is present in said bait in an amount of from about 0.00001 g to about 20 g per 100 square meters.*

26. [The method according to claim 25, wherein said compound of formula (I) is offered in an amount of from about 1.0001 g to about 1 g per 100 square meters.] *The method according to claim 23, wherein said compound is present in said bait in an amount of from about 0.001 g to about 1 g per 100 square meters.*

27. [The method according to claim 18, wherein the food source comprisng said compound of formula (I) comprises from about 0.001 to about 15% w/w of compound of formula (I).] *The method according to claim 23, wherein said bait comprises from about 0.001 to about 15% w/w of said compound.*

28. [The method according to claim 27, wherein the food source comprising said compound of formula (I) comprises from about 0.1 to about 6% w/w of compound of formula (I).] *The method according to claim 27, wherein said bait comprises from about 0.1 to about 6% w/w of said compound.*

* * * * *